United States Patent [19]
Neuss et al.

[11] 3,968,113

[45] July 6, 1976

[54] CONVERSION OF LEUROSINE TO VINCATHICINE

[75] Inventors: Norbert Neuss; Susan S. Tafur, Indianapolis, Ind.

[73] Assignee: Eli Lilly and Company, Indianapolis, Ind.

[22] Filed: Feb. 7, 1975

[21] Appl. No.: 547,895

[52] U.S. Cl. .......................................... 260/287 P
[51] Int. Cl.² .................................... C07D 215/14
[58] Field of Search ............................ 260/287 P

[56] References Cited
UNITED STATES PATENTS
3,884,976   5/1975   Bernauer et al. .................. 424/274

Primary Examiner—Sam Rosen
Attorney, Agent, or Firm—James L. Rowe; Everet F. Smith

[57] ABSTRACT

Leurosine is converted to vincathicine by treatment with acid.

4 Claims, No Drawings

CONVERSION OF LEUROSINE TO VINCATHICINE

BACKGROUND OF THE INVENTION

Several naturally-occurring alkaloids obtainable from *Vinca rosea* have been found active in the treatment of experimental malignancies in animals. Among these are leurosine (U.S. Pat. No. 3,379,057), vincaleukoblastine (vinblastine or VLB) (U.S. Pat. No. 3,097,137), leurosidine (vinrosidine) and leurocristine (VCR or vincristine) (both in U.S. Pat. No. 3,205,220). Two of these alkaloids, VLB and vincristine, are now marketed as drugs for the treatment of malignancies, particularly the leukemias and related diseases, in humans. Of these marketed compounds, vincristine is a most active and useful agent in the treatment of leukemias but is also the least abundant of the anti-neoplastic alkaloids of *Vinca rosea*.

Other dimeric indole alkaloids which have been isolated in small quantities from *Vinca rosea*, but which are less active antimitotically than VLB and vincristine, include leurocolombine, vincadioline, leuroformine, isoleurosine (deoxy VLB B) and vincathicine — see Svoboda and Barnes, *J. Pharm. Sec.*, 53, 1227 (1964). Vincathicine is not as active in treating experimental malignancies in animals as leurocristine or VLB. However, the compound is much less toxic than either of the two more potent alkaloids and there is thus a more favorable therapeutic ratio available in its use. Vincathicine was obtained originally by Svoboda and Barnes (loc. cit.) in an extremely small quantity — 7.8 grams of sulfate from 3659 grams of the chloroform eluate of postleurocristine material from the B fraction isolated from a benzene extract of leaf.

It is an object of this invention to provide a process for the partial synthesis of vincathicine from a readily available alkaloid and thus to obtain sufficient vincathicine not only for further studies of the use of the compound in the treatment of malignancies in animals, but also as a starting material for the preparation of more active anti-mitotic derivatives.

SUMMARY OF THE INVENTION

In fulfillment of the above and other objects, this invention provides a process for the preparation of vincathicine by treatment of leurosine with acid. Aqueous acid permissibly diluted with alcohol; for example, methanolic hydrogen chloride, can be employed in the conversion of leurosine to vincathicine. We prefer to use a dilute mineral acid such as aqueous sulfuric, aqueous hydrochloric, aqueous phosphoric and the like, usually diluted with a lower alkanol.

The process of this invention is more fully illustrated by the following reaction scheme:

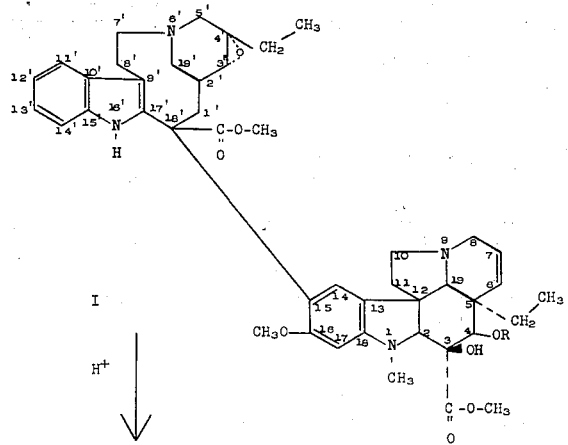

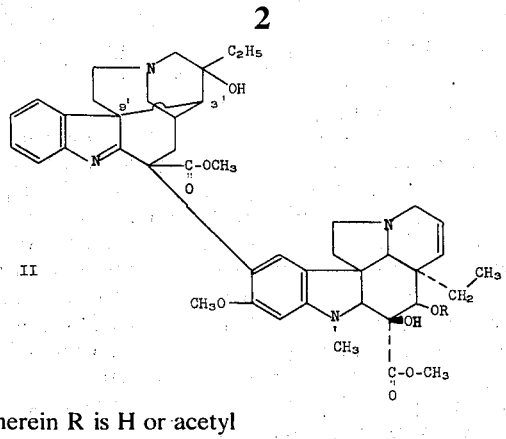

wherein R is H or acetyl

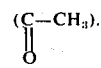

According to the above reaction scheme, leurosine, the compound of formula I in which R is acetyl, is converted by treatment with acid to vincathicine, the compound of formula II wherein R is acetyl. A small amount of 4-desacetylvincathicine (formula II wherein R is H) is also formed during the reaction and can be isolated by chromatography or the like. 4-Desacetylvincathicine is useful as an intermediate in that it can be acetylated by the procedure of Hargrove, Lloydia, 27, 340 (1964) to provide vincathicine. According to this procedure, the 3,4-diacetyl product of the reaction of the 4-desacetyl vincathicine with the acetylating agent is preferentially hydrolyzed at the 3 position by stirring with wet silica gel to provide vincathicine or other 4-acetyl derivative.

In carrying out the reaction of this invention outlined above, we prefer to use a strong mineral acid to catalyze the conversion of leurosine to vincathicine. A large range of acids, acid strengths, dilutions and co-solvents can be employed. In general, the higher the acid strength, the more rapid the reaction and the greater the amount of 4-desacetyl vincathicine produced as a by-product. However, by judicious selection of temperature and/or acid, both reaction rates can be slowed; i.e. at colder temperatures, an acid of a given strength will give a slower reaction time than at a higher temperature; at the same temperature, an acid of lesser acid strength will give a slower reaction or less by-product. Among the strong mineral acids, which we employ are included nitric acid, hydrochloric acid, perchloric acid, sulfuric acid, phosphoric acid, hydrobromic acid and the like. We prefer to use a mineral acid having an acidity constant Ho as defined by Hammett, *Physical Organic Chemistry*, page 267 (McGraw-Hill Book Co., New York 1941) of +0.83 or less. At 25°C. in aqueous solution, Paul and Long, *Chem. Rev.*, 57 1 (1957) list a number of acidity constants for strong mineral acids at various dilutions starting with 0.1 moles per liter. An acid at a given dilution having an acidity constant Ho less than +0.83 can be employed in purely aqueous solution or, using the same concentration, in a mixed solvent. The diluting solvent as previously stated can be a lower alkanol such as methanol or ethanol. Solvents containing an acid catalyst for the conversion of leurosine to vincathicine can conveniently be mixtures as 1 percent ethanolic sulfuric acid or 2 percent methanolic hydrochloric acid. Such solutions are prepared by adding 1 percent by weight of aqueous concentrated sulfuric acid to 1 l. of ethanol or by adding 2 percent by weight of 12 N hydrochloric acid to methanol. The presence of the non-aqueous, water-miscible solvent speeds up the solubilization of the basic leurosine in the acidic medium and thus cuts down the total contact time of the leurosine or vincathicine in the acidic medium and thereby decreases the amount of certain undesirable by-products. The reaction of this invention is ordinarily carried out by adding leurosine to the acidic medium at ambient temperature, stirring or shaking the mixture until the leurosine has been completely solubilized and then quenching the reaction by adding a base such as ammonium hydroxide. Vincathicine thus produced is isolated from the alkalinized reaction mixture by extraction with a water-immiscible organic solvent such as chloroform. Vincathicine is separated from leurosine and other products by chromatography with or without the added help of a gradient pH separation procedure. 4-Desacetylvincathicine, if present, is purified in similar fashion.

Some of the chemical and physical properties of vincathicine are set forth in the aforementioned article by Svoboda and Barnes (loc. cit.). In tests against transplanted tumors in mice, vincathicine, as the sulfate salt, yielded 86 and 132 percent prolongation of life in mice inoculated with lethal doses of p-1534 leukemia at vincathicine dose levels of 80 and 90 mg/kg of mouse weight respectively. The compound also showed prolongation of life in mice inoculated with Freund Ascites tumor, B-22 A leukemia, Ridgeway osteogenic sarcoma and Gardner lymphosarcoma at dose levels of 50 mg/kg. Vincathicine as a sulfate salt has also been found to be effective in treating p-1534 leukemia transplanted in DBA/2 mice at dose levels from 50 to 90 mg/kg although the percent prolongation tends to vary with the particular lot tested. The acute toxicity of vincathicine sulfate in fasted mice dosed by the intravenous route was as follows: $LD_{50}$ = about 257 mg/kg.

This invention is further illustrated by the following specific examples.

EXAMPLE 1

About 30 ml. of water was chilled to about 0°C. in an ice bath. 20 G. of 18 M sulfuric acid were added carefully with thorough mixing. Next, 500 mg. of leurosine free base were added to the acidic solution. The reaction mixture was stirred until all of the leurosine had dissolved. At this point, the reaction mixture was made basic with 12 N ammonium hydroxide. Alkali-insoluble material was extracted with chloroform. Two more chloroform extracts were obtained and the three extracts combined. The chloroform solution was dried and the chloroform removed by evaporation in vacuo. The above process was repeated and a yield of 368 mg. of alkaloidal free bases obtained after evaporation of the chloroform. The free bases were chromatographed over grade 2 alumina using benzene as a solvent. Three fractions obtained by elution with 45 ml. of benzene and single 35 ml. fractions obtained by elution with 99:1, 19:1, and 9:1 benzene chloroform mixtures respectively were collected and discarded as were five fractions eluted with a total of 105 ml. of a 3:1 benzene chloroform mixture, and four fractions eluted with 100 ml. of 1:1 benzene chloroform mixture. Eleven 25 ml. fractions eluted with a 1:1 benzenechloroform solvent mixture were then collected and combined. The total weight of alkaloid recovered after evaporation of the eluting solvent was 195.7 mg. The alkaloidal material was rechromatographed over florisil using 100 percent ethyl acetate as a solvent. Six fractions eluted with 60 ml. of ethyl acetate were collected and discarded. The next two fractions, each eluted with 50 ml. of ethyl acetate, were collected and combined. Evaporation of the ethyl acetate yielded 26 mg. of vincathicine.

Vincathicine thus prepared has the following spectral characteristics: mass spectrum: $M^+$ 808, 750, 469, 282, 168, 135, 122, 121, 107. pmr spectrum: (100 $MH_z$)

| Assignment | Chemical Shift* |
|---|---|
| HO-3 | 9.52 |
| H-11' H-14' | 7.59 |
| H-13' | 7.28 |
| H-12' | 7.24 |
| H-14 | 6.43 |
| H-17 | 6.08 |
| H-7 | 5.81 |
| H-4 | 5.41 |
| H-6 | 5.25 |
| $CH_3O$-16 | 3.77 |
| $COOCH_3$ | 3.76 |
| H-2 | 3.68 |
| $COOCH_3$ | 3.65 |
| $N-CH_3$ | 2.68 |
| $OCOCH_3$ | 2.05 |
| $CH_3$-21, $CH_3$-21' | 0.55 |

*in ppm ($\delta$) downfield from internal TMS

Vincathicine sulfate had the following U.V. spectrum: $\lambda_{max}^{EtoH}$ = 300; 264; 213.

EXAMPLE 2

A solution was prepared by dissolving 50 mg. of leurosine in 37.5 ml. of 2 percent methanolic hydrogen chloride. The solution was heated to refluxing temperature for 30 minutes, after which time 30 ml. of water was added and the methanol removed by evaporation in vacuo. The acidic aqueous solution was made basic with 15 N ammonium hydroxide. The alkaline insoluble material was extracted with chloroform. Three extracts were obtained and these extracts were combined, dried and the chloroform removed by evaporation to dryness in vacuo. Thin layer chromatography indicated the presence of vincathicine in the residual alkaloids. The residue was chromatographed over preparative thin layer chromatography plates using a 3:1 ethyl acetate anhydrous ethanol solvent mixture as the eluant. Five bands were obtained. Band 4 was vincathicine and Band 5 4-desacetylvincathicine. Bands 4 and 5 were scraped from the plate and the alkaloids eluted separately therefrom with chloroform. Vincathicine and 4-desacetylvincathicine were obtained by evaporation of their respective chloroform eluants to dryness.

4-Desacetylvincathicine thus prepared has the following physical characteristics: mass spectrum: $M^+$ 766, 708, 649, 427, 353, 240, 185, 168, 135, 122, 121, 107. U.V. spectrum: $\lambda_{max}^{EtoH}$ = 310 (shoulder); 265 ($a_m$ = 16,510); 215 ($a_m$ = 42,200). pmr spectrum: (100 $MH_z$)

| Assignment | Chemical Shift* |
|---|---|
| HO-3 | 9.47 |
| H-11', H-14' | 7.58 |
| H-13' | 7.32 |
| H-12' | 7.20 |
| H-14 | 6.45 |
| H-17 | 6.07 |
| H-7, H-6 | 5.77 |
| H-4 | 4.01 |
| $CH_3O$-16 | 3.82 |
| $COOCH_3$ | 3.74 |
| $COOCH_3$ | 3.66 |
| $N-CH_3$ | 2.73 |
| $CH_3$-21, $CH_3$-21' | 0.62 |

*in ppm ($\delta$) downfield from internal TMS

EXAMPLE 3

About 5 g. of leurosine were added to a solvent mixture containing 150 ml. of 12 N hydrochloric acid and 1000 ml. of methanol. The resulting solution was refluxed for 20 minutes after which time another 1000 ml. of water were added and the methanol removed by evaporation in vacuo. The acidic reaction mixture was made alkaline by the addition of 15 N ammonium hydroxide. Alkali-insoluble material was extracted with four 500 ml. portions of chloroform. The chloroform extracts were combined, dried and the chloroform removed by evaporation in vacuo. A gradient pH purification procedure was employed to separate vincathicine from leurosine and other contaminants. (See Svoboda, U.S. Pat. No. 3,205,220, column 3, line 70, et seq. and column 6, line 65 et seq.) In this procedure, the residual alkaloids were dissolved in 250 ml. of 2.1 percent aqueous citric acid and fractions were obtained by extracting the citric acid solution at gradually increasing pH's. Benzene extracts were obtained at pH = 2.75, 3.4, 3.9, 4.4, 4.9, 5.4, 5.9, 6.6, 7.5, the fractions obtained at pH = 5.4 and 5.9 weighing 1.29 grams were combined. 60 Mg. of the combined fractions were subjected to preparative thin layer chromatography developed in a 3:1 ethyl acetate-anhydrous ethanol solvent mixture. Two bands were obtained. Band 2 was vincathicine. The vincathicine zone was scraped from the plate and the vincathicine eluted with a methanol-chloroform solvent mixture. Vincathicine was also obtained from the combined gradient pH fractions obtained at 6.4 to 7.5. Here vincathicine was in Band 1 and desacetyl vincathicine was isolated from Band 4.

EXAMPLE 4

Vincathicine sulfate was prepared by dissolving vincathicine in anhydrous ethanol and adjusting the pH to about 2.9–4.0 with 1–2 percent sulfuric acid in anhydrous ethanol. Evaporation of the solvent in vacuo yielded vincathicine sulfate.

We claim:

1. The process which comprises the essential steps of heating leurosine with mineral acid in an aqueous solvent and isolating the vincathicine thus formed.

2. A process according to claim 1 in which the aqueous mineral acid employed has a Hammet acidity constant Ho of +0.83 or less.

3. A process according to claim 1 in which the aqueous solvent is a mixture of water and a water-miscible alkanol or a water-miscible alkanoic acid.

4. A process according to claim 1 in which methanolic hydrochloric acid is used as the mineral acid.

* * * * *